United States Patent
Wang et al.

(10) Patent No.: US 11,666,523 B2
(45) Date of Patent: Jun. 6, 2023

(54) AQUEOUS ORAL CARE FLUORIDE TREATMENT COMPOSITIONS, AND METHODS

(71) Applicant: 3M INNOVATIVE PROPERTIES COMPANY, St. Paul, MN (US)

(72) Inventors: Yizhong Wang, Woobury, MN (US); Tiffany T. Ton, Woodbury, MN (US); Carola A. Carrera Vidal, Plymouth, MN (US); Joel D. Oxman, Minneapolis, MN (US); Jennifer J. Post, St. Paul, MN (US); Paul R. Klaiber, Mahtomedi, MN (US)

(73) Assignee: 3M INNOVATIVE PROPERTIES COMPANY, St. Paul, MN (US)

(*) Notice: Subject to any disclaimer, the term of this patent is extended or adjusted under 35 U.S.C. 154(b) by 0 days.

(21) Appl. No.: 16/644,415

(22) PCT Filed: Aug. 22, 2018

(86) PCT No.: PCT/IB2018/056366
§ 371 (c)(1),
(2) Date: Mar. 4, 2020

(87) PCT Pub. No.: WO2019/048962
PCT Pub. Date: Mar. 14, 2019

(65) Prior Publication Data
US 2020/0197289 A1    Jun. 25, 2020

Related U.S. Application Data

(60) Provisional application No. 62/556,095, filed on Sep. 8, 2017.

(51) Int. Cl.
*A61K 8/81* (2006.01)
*A61K 8/21* (2006.01)
*A61K 8/73* (2006.01)
*A61Q 11/00* (2006.01)

(52) U.S. Cl.
CPC .............. *A61K 8/8147* (2013.01); *A61K 8/21* (2013.01); *A61K 8/73* (2013.01); *A61Q 11/00* (2013.01); *A61K 2800/5426* (2013.01); *A61K 2800/56* (2013.01)

(58) Field of Classification Search
CPC .......... A61K 8/8147; A61K 8/21; A61K 8/73; A61K 2800/5426; A61K 2800/56; A61K 8/731; A61K 8/8152; A61K 8/8182; A61K 8/84; A61K 8/24; A61K 8/8158; A61K 33/16; A61Q 11/00
See application file for complete search history.

(56) References Cited

U.S. PATENT DOCUMENTS

| | | | |
|---|---|---|---|
| 4,837,007 A | 6/1989 | Duckworth | |
| 5,211,559 A | 5/1993 | Hart | |
| 8,968,709 B2 | 3/2015 | Yang | |
| 2009/0117507 A1* | 5/2009 | Abolfathi | A61C 19/063 433/6 |
| 2011/0236859 A1* | 9/2011 | Keleman | A61K 8/66 433/216 |
| 2014/0369953 A1* | 12/2014 | Purschwitz | A01N 31/16 424/78.36 |
| 2016/0220472 A1* | 8/2016 | Wang | A61K 8/8152 |

FOREIGN PATENT DOCUMENTS

| | | |
|---|---|---|
| JP | 2000-034213 | 2/2000 |
| JP | 2008-201704 A | 9/2008 |
| JP | 2011-020980 A | 2/2011 |
| JP | 2011-126840 A | 6/2011 |
| JP | 2013-067567 A | 4/2013 |
| WO | WO 2004-054530 | 7/2004 |
| WO | WO 2015-038400 | 3/2015 |
| WO | WO 2015-038580 | 3/2015 |
| WO | WO 2015-160762 | 10/2015 |
| WO | WO 2018-148134 | 8/2018 |

OTHER PUBLICATIONS

Colgate Palmolive, "Alcohol-Free Sensitive Mouthwash", Record ID 4756793, Apr. 2017,3 pages, XP055521335A.
Database WPI Week 200017, Apr. 1, 2000 Thomson Scientific, London, GB; AN 2000-190093 XP002786322, Akaha Y; Hayashi R, Hiratsuka S, Composition for oral cavity—used in Eradication of bacteria in oral cavity & JP 2000 034213 A (Lion Corp) Feb. 2, 2000, abstract, 1 page.
Elevate Oral Care, "FluoriMax25% NaF Varnish", Safety Data Sheet, ECO 1023, Rev. 00 Aug. 2015, 7 pages, XP055521775A.
Monograph, "Topical Fluoride Preparations for Reducing Incidence of Dental Caries," Federal Register, May 14, 1974, vol. 39, No. 94, 1 page.
International Search Report for PCT International Application No. PCT/IB2018/056366, dated Dec. 7, 2018, 5 pages.

* cited by examiner

*Primary Examiner* — Robert A Wax
*Assistant Examiner* — Quanglong N Truong
(74) *Attorney, Agent, or Firm* — 3M Innovative Properties Company

(57) ABSTRACT

An aqueous oral care fluoride treatment composition, a method of providing fluoride to a patients tooth surface, and a method of reducing the incidence of dental caries, wherein the composition includes: 0.5 wt-% to 4.8 wt-% of a water-soluble cationic N-containing polymer; a pharmaceutically acceptable buffer; 1.0 wt-% to 2.5 wt-% of sodium fluoride; and at least 60 wt-% water; wherein the weight percentages are based on the total weight of the aqueous composition.

21 Claims, No Drawings

AQUEOUS ORAL CARE FLUORIDE TREATMENT COMPOSITIONS, AND METHODS

BACKGROUND

Fluoride treatment involves the application of fluoride to a tooth surface with the formation of fluorapatite and calcium fluoride.

There are two major in-office fluoride treatment methods currently in use. One treatment method uses a fluoride gel/foam in a tray. This method requires several grams of fluoride gel stored in a tray that is then placed into a patient's mouth onto the teeth. This tray is left in the mouth with the gel/foam in contact with the teeth for 1 to 4 minutes. The gel/foam formulation is an aqueous system that includes 2% sodium fluoride. This material requires the use of suction to pull the extra gel out of the mouth to avoid unnecessary high amounts of fluoride ingestion.

Another treatment method is a dental fluoride varnish. Most fluoride varnishes on the market are rosin/ethanol based formulations with a hydrophobic nature. The varnish is painted on the teeth and remains in place for several hours to allow for the fluoride to be released from the composition. Typically, dentists use fluoride varnishes for in-office fluoride treatment. Most dental fluoride varnishes include 5% sodium fluoride. The dose of varnish is about 0.5 gram. Dental varnishes place much smaller amounts of fluoride into a patient's mouth compared to fluoride gel/foams. Thus, fluoride ingestion is less with fluoride varnishes. Also, fluoride varnishes are easier to apply as they are simply painted on a patient's teeth; however, fluoride varnish treatments are more labor intensive than gel treatments and fluoride varnish treatments leave the patient with an unpleasant "dirty teeth" feeling.

Compositions that are as simple to apply to teeth as varnishes and work in time periods as short as gel/foam formulations are desired.

SUMMARY OF THE DISCLOSURE

The present disclosure provides aqueous oral care fluoride treatment compositions and methods of treating (i.e., methods of providing fluoride to a patient's tooth surface).

Such compositions can be used as in-office fluoride treatment compositions. They can be formulated into a composition that can be painted on a tooth surface if desired. They can provide similar fluoride efficacy to that of varnishes in the shorter periods of time of gel/foam formulations.

In one embodiment, the present disclosure provides an aqueous oral care fluoride treatment composition that includes: 0.5 wt-% to 4.8 wt-% of a water-soluble cationic nitrogen-containing (N-containing) polymer; a pharmaceutically acceptable buffer; 1.0 wt-% to 2.5 wt-% of sodium fluoride; and at least 60 wt-% water; wherein the weight percentages are based on the total weight of the aqueous composition.

In another embodiment, the present disclosure provides a method of providing fluoride to a patient's tooth surface. The method involves applying an aqueous oral care fluoride treatment composition as disclosed herein to the patient's tooth surface.

In another embodiment, the present disclosure provides a method of reducing the incidence of dental caries. The method involves applying an aqueous oral care fluoride treatment composition as disclosed herein to the patient's tooth surface.

The terms "polymer" and "polymeric material" include, but are not limited to, organic homopolymers, copolymers, such as for example, block, graft, random, and copolymers, terpolymers, etc., and blends and modifications thereof. Furthermore, unless otherwise specifically limited, the term "polymer" shall include all possible geometrical configurations of the material. These configurations include, but are not limited to, isotactic, syndiotactic, and atactic symmetries.

The term "comprises" and variations thereof do not have a limiting meaning where these terms appear in the description and claims. Such terms will be understood to imply the inclusion of a stated step or element or group of steps or elements but not the exclusion of any other step or element or group of steps or elements. By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements.

The words "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure.

In this application, terms such as "a," "an," and "the" are not intended to refer to only a singular entity, but include the general class of which a specific example may be used for illustration. The terms "a," "an," and "the" are used interchangeably with the phrases "at least one" and "one or more." The phrases "at least one of" and "comprises at least one of" followed by a list refers to any one of the items in the list and any combination of two or more items in the list.

The term "or" is generally employed in its usual sense including "and/or" unless the content clearly dictates otherwise.

The term "and/or" means one or all of the listed elements or a combination of any two or more of the listed elements.

Also herein, all numbers are assumed to be modified by the term "about" and in certain embodiments, preferably, by the term "exactly." As used herein in connection with a measured quantity, the term "about" refers to that variation in the measured quantity as would be expected by the skilled artisan making the measurement and exercising a level of care commensurate with the objective of the measurement and the precision of the measuring equipment used. Herein, "up to" a number (e.g., up to 50) includes the number (e.g., 50).

Also herein, the recitations of numerical ranges by endpoints include all numbers subsumed within that range as well as the endpoints (e.g., 1 to 5 includes 1, 1.5, 2, 2.75, 3, 3.80, 4, 5, etc.).

The term "room temperature" refers to a temperature of 20° C. to 25° C. or 22° C. to 25° C.

Reference throughout this specification to "one embodiment," "an embodiment," "certain embodiments," or "some embodiments," etc., means that a particular feature, configuration, composition, or characteristic described in connection with the embodiment is included in at least one embodiment of the disclosure. Thus, the appearances of such phrases in various places throughout this specification are not necessarily referring to the same embodiment of the disclosure. Furthermore, the particular features, configurations, compositions, or characteristics may be combined in any suitable manner in one or more embodiments.

The above summary of the present disclosure is not intended to describe each disclosed embodiment or every implementation of the present disclosure. The description that follows more particularly exemplifies illustrative embodiments. In several places throughout the application, guidance is provided through lists of examples, which examples may be used in various combinations. In each instance, the recited list serves only as a representative group and should not be interpreted as an exclusive list.

DETAILED DESCRIPTION OF ILLUSTRATIVE EMBODIMENTS

The present disclosure provides aqueous oral care fluoride treatment compositions. The present disclosure also provides methods of providing fluoride to a patient's tooth surface, as well as methods of reducing the incidence of dental caries. Such methods involve applying an aqueous oral care fluoride treatment composition as described herein to the patient's tooth surface.

In certain embodiments, applying an aqueous oral care fluoride treatment composition includes painting the treatment composition on the patient's tooth surface.

In certain embodiments, applying an aqueous oral care fluoride treatment composition includes dispensing the treatment composition into a dental tray and attaching the tray having the treatment composition therein to the patient's tooth surface. In certain embodiments, the dental tray includes an orthodontic aligner treatment tray.

Aqueous oral care fluoride treatment compositions of the present disclosure include at least 60 wt-%, at least 70 wt-%, or at least 80 wt-%, water, based on the total weight of the aqueous composition. In certain embodiments, a treatment composition includes up to 96 wt-%, or up to 90 wt-%, water, based on the total weight of the aqueous composition.

Treatment compositions of the present disclosure are aqueous compositions. Although they may include a small amount of organic solvent (e.g., (C1-C4) alcohols such as ethanol), preferably they are free of organic solvents that function as liquid carriers (as opposed to organic solvents that are used as carriers/solvents for flavorants or sweeteners). For example, certain additives may be provided as a solution or dispersion in an organic solvent as a liquid carrier. If there is any organic solvent (that functions as a liquid carrier) present in aqueous oral care fluoride treatment compositions of the present disclosure, it is present in an amount of less than 5 wt-%, based on the total weight of the aqueous composition.

Aqueous oral care fluoride treatment compositions of the present disclosure include a pharmaceutically acceptable buffer. The type and amount of such buffer is selected to provide a treatment composition with a pH of at least 6, or at least 6.5. In certain embodiments, the type and amount of such buffer is selected to provide a treatment composition with a pH of up to 8, up to 7.5, or up to 7. In certain embodiments, the type and amount of such buffer is selected to provide a treatment composition with a pH of 6.5 to 7.5, or a pH of 7.0, particularly for methods of reducing the incidence of dental caries, according to the Monograph entitled "Topical Fluoride Preparations for Reducing Incidence of Dental Caries," Federal Register, Vol. 39, No. 94, May 14, 1974.

Water-Soluble Polymers

Aqueous oral care fluoride treatment compositions of the present disclosure include a water-soluble polymer; however, typically the compositions are not gels. In general, gels include polymer chains that are chemically crosslinked and extended or swollen by solvents (e.g., water). Thus, typically, compositions of the present disclosure are not crosslinked, although they may include polymer chains that have non-chemically bonded linkages that are extended in the presence of a solvent (e.g., water).

Aqueous oral care fluoride treatment compositions of the present disclosure include a water-soluble cationic N-containing polymer. Typically, herein a water-soluble cationic N-containing polymer has a solubility in water at room temperature of greater than 1 gram, greater than 2 grams, greater than 3 grams, greater than 4 grams, or greater than 5 grams, per 100 grams of water.

In certain embodiments, an aqueous oral care fluoride treatment composition of the present disclosure includes a water-soluble cationic N-containing polymer in an amount of at least 0.5 wt-%, or at least 0.6 wt-%, or at least 0.9 wt-%, based on the total weight of the aqueous composition. In certain embodiments, an aqueous oral care fluoride treatment composition of the present disclosure includes a water-soluble cationic N-containing polymer in an amount of up to 4.8 wt-%, or up to 4.0 wt-%, based on the total weight of the aqueous composition.

In certain embodiments, suitable water-soluble cationic N-containing polymers may not be cationic, may not be water soluble, or may not be either, prior to incorporation into a treatment composition. Such polymers are referred to as "polymer precursors" herein. For example, a water-insoluble basic polymer (e.g., EUDRAGIT E100 poly(butyl methacrylate-co-(2-dimethylaminoethyl) methacrylate-co-methyl methacrylate copolymer) may become cationic upon contact with an acidic aqueous solution. Typically, upon forming a cationic polymer, such polymers have a water solubility at room temperature of greater than 1 gram per 100 grams of water.

Examples of classes of suitable water-soluble cationic N-containing polymers or polymer precursors include the following: (meth)acrylate copolymers containing dimethylaminoethyl side groups, such as those copolymers derived from only (meth)acrylate monomers or those copolymers derived from (meth)acrylate monomers and other monomers such as vinyl monomers; polyethylenimines; and cationic-modified polysaccharides. These polymers may include nitrogen in the backbone and/or side groups. Various combinations of such polymers can be used if desired.

Typically, the (meth)acrylate copolymers with dimethylaminoethyl side groups are polymer precursors. The dimethylamioethyl side groups of the (meth)acrylate copolymers can be reacted with other chemicals (e.g., acids such as citric acid or buffers containing an acidic component) to form cationic side groups. Evonik EUDRAGIT E100 poly (butyl methacrylate-co-(2-dimethylaminoethyl) methacrylate-co-methyl methacrylate copolymer is an example of such a polymer. A copolymer of 2-dimethylaminoethyl (meth)acrylate (DMAEMA) and vinyl pyrrolidone (VP) available as VP/DMAEMA copolymer 845G from Ashland Chemical is another example of this type of polymer.

Polyethyleneimine polymers contain nitrogen atoms in both the polymer backbone and the side groups. Polyethylenimine polymers can include either linear or branched chains and can be transformed into a water-soluble cationic polymer. A typical example of a polyethylenimine (PEI) is that available from Polyscience.

Cationic-modified polysaccharides include cationic side groups attached to a polysaccharide. Accordingly, they are cationic and water-soluble without further treatment. A typical example of such polymer is that available as Poly-sugaQuat-1218P from Colonial Chemical.

Examples of suitable water-soluble cationic N-containing polymers or polymer precursors include the following:

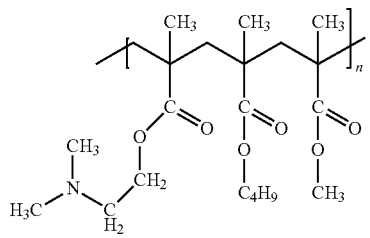

which is a (meth)acrylate copolymer containing dimethyl-aminoethyl side groups, wherein n represents the number of repeat units (typically n=50-2,000) (an example of which is poly(butyl methacrylate-co-(2-dimethylaminoethyl) methacrylate-co-methyl methacrylate with a monomer mole ratio of 1:2:1 and an approximate average molecular weight (weight average) within a range of 5,000 to 500,000 grams/mole, such as 47,000 grams/mole);

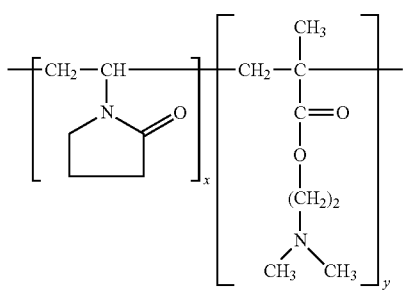

which is a (meth)acrylate copolymer containing dimethyl-aminoethyl side groups, wherein x and y represent the number of repeat units (typically x=200-20,000, and y=200-20,000) (an example of which is VP/DMAEMA copolymer 845G from Ashland Chemical having an approximate average molecular weight (weight average) within a range of 700,000 grams/mole to 1,200,000 grams/mole);

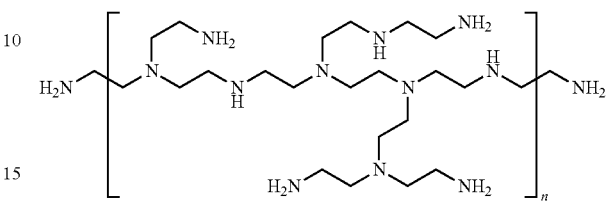

which is a polyetheneimine, wherein n represents the number of repeat units (typically n=200-20,000) (an example of which is a PEI with an approximate average molecular weight (weight average) within a range of 5,000 grams/mole to 1,000,000 grams/mole, such as 10,000);

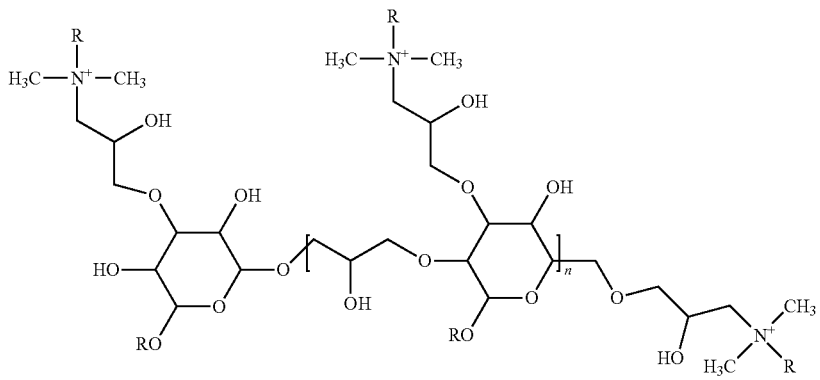

which is a cationic-modified polysaccharide, wherein n represents the number of repeat units (typically n=10-1000) (an example of which is PolySugaQuat-1218P from Colonial Chemical that has a viscosity of 1300CP at 30% solid in water solution); and combinations of any of the above.

In certain embodiments, the cationic polymer may have some hydrogen bonding interactions with thickeners (e.g., a hydroxyethyl cellulose) to form a sufficiently viscous aqueous composition.

Active Agent—Sodium Fluoride

Aqueous oral care fluoride treatment compositions of the present disclosure include sodium fluoride as the active agent. In certain embodiments, a treatment composition includes at least 1.0 wt-%, based on the total weight of the aqueous composition. In certain embodiments, a treatment composition includes up to 2.5 wt-%, based on the total weight of the aqueous composition.

In use, the fluoride releasing composition can be applied to the oral cavity. In one embodiment, the fluoride releasing composition is typically applied directly to one or more teeth. The fluoride releasing composition is typically maintained in contact with the teeth for a sufficient time to release a therapeutically effective amount of fluoride. The release of fluoride from the fluoride releasing composition can be measured, for example, by the method described in the Examples Section of this disclosure. In certain embodiments, a treatment composition of the present disclosure releases at least 50% (or at least 55%, or at least 60%) of the sodium fluoride in 5 minutes or less. In certain embodiments, a treatment composition of the present disclosure releases at least 85% (or at least 90%, or at least 95%) of the sodium fluoride in 10 minutes or less. In certain embodiments, a treatment composition of the present disclosure releases at least 90% (or at least 95%, or at least 99%) of the sodium fluoride in 20 minutes or less.

In certain embodiments, a treatment composition of the present disclosure releases no greater than 90% (or no greater than 88%, or no greater than 70%) of the sodium fluoride in 1 minute or less. In certain embodiments, a treatment composition of the present disclosure releases no greater than 95% (or no greater than 92%, or no greater than 75%) of the sodium fluoride in 3 minutes or less. In certain embodiments, a treatment composition of the present disclosure releases no greater than 98% (or no greater than 95%, or no greater than 80%) of the sodium fluoride in 5 minutes or less.

In certain embodiments, a treatment composition of the present disclosure releases 100% (or no greater than 98%, or no greater than 90%) of the sodium fluoride in 10 minutes or less. In certain embodiments, a treatment composition of the present disclosure releases 100% (or no greater than 99%, or no greater than 95%) of the sodium fluoride in 15 minutes or less. In certain embodiments, a treatment composition of the present disclosure releases 100% (or no greater than 99%, or no greater than 98%) of the sodium fluoride in 20 minutes or less.

Additional Optional Active Agents

Aqueous oral care fluoride treatment compositions of the present disclosure can also contain one or more active agents in addition to sodium fluoride. When included, the one or more additional active agents usually, but not always, include one or more active agents that are active in the oral cavity against disorders, diseases, or conditions of the teeth, gums, cheeks, tongue, roof of the mouth, and the like.

Examples of additional active agents that can be employed include one or more whitening agents, anti calculus agents, remineralization agents, stannous sources, antimicrobial agents, antioxidants, saliva stimulating agents, breath freshening agents, antiplaque agents, anti-inflammatory agents, $H_2$ antagonists, desensitizing agents, nutrients, and proteins. Various combinations of such additional active agents may be used if desired. When employed, one or more additional active agents will be typically used in amounts sufficient to achieve their intended effect.

When employed, the whitening agents can be a wide variety of suitable whiting agents. The whitening agents can include, for example, a peroxide whitening agent, a non-peroxide whitening agent, or both. Peroxide whitening agents include hydrogen peroxide, peroxide of alkali or alkaline earth metals, such as sodium peroxide, potassium peroxide, lithium peroxide, magnesium peroxide, calcium peroxide, barium peroxide, and the like, glyceryl hydrogen peroxide, alkyl hydrogen peroxide, dialkyl peroxide, peroxy acids or peroxy acid salts, benxoyl peroxide, urea peroxide, and the like. Hydrogen peroxide is most common. Non-peroxide whitening agents include chlorine dioxide, chlorites, and hypochlorites. Chlorites and hyperchlorites are typically in the form of alkali or alkaline earth metal salts, such as salts of lithium, potassium, sodium, magnesium, calcium, or barium. Colorants, titanium dioxide, and hydroxyapatite can also be used.

When employed, the anticalculus agents can be a wide variety of suitable anticalculus agents. The anticalculus agents can include, for example, phosphates, polyphosphates, such as pyrophosphates, polyolefin sulfonates, polyolefin phosphates, diphosphonates, phosphonoalkane carboxylic acids, and salts thereof, typically alkali metal or ammonium salts.

When employed, the remineralization agents can be a wide variety of suitable remineralization agents. The remineralization agents can include, for example, materials that release calcium ions, phosphorous-containing ions, or both, such as calcium phosphate (e.g., mono-, di-, and/or tricalcium phosphate), hydroxyapatite, calcium carbonate, and the like.

Examples of materials that release calcium ions are calcium salts that are water soluble, such as those selected from calcium chloride, calcium nitrate, calcium gluconate, calcium lactate gluconate, calcium acetate, hydrates thereof, and combinations thereof. In certain embodiments, the calcium salt is selected from calcium chloride, calcium nitrate, hydrates thereof, and combinations thereof.

A calcium salt can also be used to modulate the fluoride release profile.

In certain embodiments, a calcium salt is present in an amount of at least 0.5 wt-%, based on the total weight of the aqueous composition. In certain embodiments, a calcium salt is present in an amount of than 3.0 wt-%, less than 2.0 wt-%, or less than 1.5 wt-%, based on the total weight of the aqueous composition.

When employed, the stannous sources can be a wide variety of suitable source of stannous ions. The stannous ion sources can include, for example, stannous halides, organic stannous carboxylate salts, such as stannous formate, stannous acetate, stannous gluconate, stannous lactate, stannous tartrate, and stannous citrate. When the fluoride source is stannous fluoride, it can also function as a stannous source.

When employed, the antimicrobial agents can include a wide variety of orally acceptable antimicrobial agents. Examples include triclosan, 8-hydroxyquinoline, zinc ion, stannous ion, cupric compounds, phthalic acid and salts thereof, quaternary ammonium compounds, sanguinarine, salicylanilide, salicylic acid, thymol, eugenol, neomycin, kanamycin, clindamycin, amoxicillin, tetracycline, doxycycline, minocycline, metronidazole, chlorhexidine, and the like.

When employed, the antioxidants can be a wide variety of orally acceptable antioxidants. Examples include butylated hydroxy anisone, butylated hydroxy toluene, vitamin A, carotenoids, vitamin E, flavonoids, polyphenols, ascorbic acid or salts thereof, chlorophyll, melatonin, and the like.

When employed, the saliva stimulants can be a wide variety of orally acceptable saliva stimulants. Examples include citric acid, lactic acid, succinic acid, ascorbic acid, adipic acid, fumaric acid, and tartaric acid.

When employed, the breath freshening agents can be a wide variety of orally acceptable breath freshening agents. Examples include zinc salts such as zinc salts of gluconate, citrate, and chlorite, alpha-ionone, and the like.

When employed, the antiplaque agents can be a wide variety of orally acceptable antiplaque agents. Examples include stannous salts, salts of copper, magnesium or strontium, dimethicone copolyols, such as cetyl dimethicone copolyol, papain, glucamylase, glucose oxidase, urea, calcium lactate, calcium glycerophosphate, strontium polyacrylates, and the like. Further examples of antiplaque agents include biofilm inhibition agents, particularly those described in U.S. Pat. No. 8,968,709 (Yang et al.).

When employed, the anti-inflammatory agents can be a wide variety of orally acceptable anti-inflammatory agents. Examples include steroids such as flucinolone and hydrocortisone, non-steroidal anti-inflammatory drugs such as ketorolac, flurbiprofen, ibuprofen, naproxen, indomethacin, diclofenac, etodolac, indomethacin, sulindac, tomlmetin, ketoprofen, fenoprofen, piroxicam, nabumetone, acetyl salicylic acid, salicylic acid, diflunisal, meclofenamate, mefenamic aicd, oxyphenbutazone, phenylbutazone, and the like.

When employed, the 1-12 antagonists can be a wide variety of orally acceptable $H_2$ antagonists. Examples include cimetidine, etinidine, ranitidine, tiotidine, lupitidine, denetidine, famotidine, roxatidine, pifatidine, lamtidine, zaltidine, nizatidine, mifentidine, ramixotidine, loxtidine, bisfentidine, sufotidine, ebrotidine, impromdine, and the like.

When employed, the desensitizing agents can be a wide variety of orally acceptable desensitizing agents. Examples include potassium citrate, potassium chloride, potassium tartrate potassium, bicarbonate, potassium oxalate, potassium nitrate, strontium salts, arginine, acetyl salicylic acid or salts thereof, salicylic acid or salts thereof, codeine, acetaminophen, and the like.

When employed, the nutrients can be a wide variety of orally acceptable nutrients. Examples include vitamins, such as vitamins C, D, thiamine, riboflavin, folic acid, nicotinamide, niacin, pyridoxine, bioflavonoids, and the like, supplements, such as amino acids, lipotropics, fish oil, polyunsaturated fatty acids, eicosapentanoic acid, docosahexanic acid, coenzyme Q10, ubiquinone, minerals such as potassium, and the like.

When employed, the proteins can include a wide variety of orally acceptable proteins. Examples include milk proteins, peroxide producing enzymes, amylase, papain, glucoamylase, glucose oxidase, and the like.

Buffers

Aqueous oral care fluoride treatment compositions of the present disclosure include a pharmaceutically acceptable buffer. The type and amount of such buffer is selected to provide a treatment composition with a pH of at least 6, or at least 6.5. In certain embodiments, the type and amount of such buffer is selected to provide a treatment composition with a pH of up to 8, up to 7.5, or up to 7. In certain embodiments, the type and amount of such buffer is selected to provide a treatment composition with a pH of 6.5 to 7.5, or a pH of 7.0. A wide variety of suitable pharmaceutically acceptable buffers can be included. Examples include acetate (e.g., sodium acetate), sodium carbonate, citrate (e.g., sodium citrate), tartrate, glycylglycine, histidine, glycine, lysine, arginine, sodium dihydrogen phosphate, disodium hydrogen phosphate, sodium phosphate, tris(hydroxymethyl)-aminomethan, or mixtures thereof.

Thickeners

In certain embodiments, aqueous oral care fluoride treatment compositions of the present disclosure include a thickener to provide a composition with a suitable viscosity to allow for the desired method of application. For example, a suitable thickener in a sufficient amount may be used to achieve a solution viscosity adequate to maintain the composition in an inverted mouthpiece tray applicator for up to about four minutes (typical time for a professionally applied fluoride treatment), and yet be fluid enough to have acceptable handling characteristics for the dental operator (e.g., when dispensing into a dental tray applicator). Or, a suitable thickener in a sufficient amount may be used to achieve a solution viscosity adequate to paint on a tooth surface.

In certain embodiments, the type and amount of thickener is selected to provide a treatment composition with a viscosity of at least 0.5 Pascal seconds at a shear rate of 1.0/second. In certain embodiments, a type and amount of thickener is selected to provide a treatment composition with a viscosity of up to 100 Pascal seconds at a shear rate of 1.0/second.

In certain embodiments, a thickener is present in a treatment composition in an amount of less than 2.5 wt-%, based on the total weight of the aqueous composition. In certain embodiments, a thickener is present in an amount of at least 0.5 wt-%, based on the total weight of the aqueous composition.

Suitable thickeners are typically those that are generally safe for human ingestion (FDA approved for internal use), do not bind fluoride ions, and do not significantly affect the bioavailability of fluoride ions.

In certain embodiments, the thickener is selected from natural gums, non-acid cellulose derivatives (e.g., hydroxyethyl cellulose), inorganic fillers (e.g., colloidal silica, fumed silica, alumina, titania, and zinc oxide), alkylene oxide polymers (e.g., polyethylene glycol, polypropylene glycol, and copolymers of polyethylene glycol and polypropylene glycol), non-acid modified starches, and combinations thereof.

Optional Additives

In certain embodiments, aqueous oral care fluoride treatment compositions of the present disclosure include one or more optional additives including flavoring agents (i.e., flavorants) and sweeteners. Various combinations of such additives may be used if desired.

In certain embodiments, aqueous oral care fluoride treatment compositions of the present disclosure include a sweetener. A wide variety of orally acceptable sweeteners can be used. Common sweeteners include xylitol, sorbitol, sucralose, aspartame, saccharin, usually sodium saccharine, and the like. When present, a sweetener can be used in any suitable amount, most often in an amount sufficient to impart a pleasant sweetness to the composition. The suitable amount is typically 0.5 wt-% to 15 wt-%, based on the total weight of the aqueous composition.

In certain embodiments, aqueous oral care fluoride treatment compositions of the present disclosure include a flavoring agent. A wide variety of orally acceptable flavoring agents can be used. Common flavoring agents include peppermint oil, spearmint oil, cherry flavor, citric acid, orange flavor, vanilla, strawberry flavor, coconut flavor, and bubble gum flavor. When present, a flavoring agent can be used in any suitable amount, most often in an amount sufficient to impart a desired flavor to the composition. The suitable amount is typically 1 wt-% to 4 wt-%, based on the total weight of the aqueous composition.

Exemplary Embodiments

Embodiment 1 is an aqueous oral care fluoride treatment composition comprising: 0.5 wt-% to 4.8 wt-% of a water-soluble cationic N-containing polymer; a pharmaceutically acceptable buffer; 1.0 wt-% to 2.5 wt-% of sodium fluoride; and at least 60 wt-% water; wherein the weight percentages are based on the total weight of the aqueous composition.

Embodiment 2 is the treatment composition of embodiment 1 wherein the water-soluble cationic N-containing polymer comprises a cationic N-containing polymer having a solubility in water of greater than 1 gram, greater than 2 grams, greater than 3 grams, greater than 4 grams, or greater than 5 grams, per 100 grams of water.

Embodiment 3 is the treatment composition of embodiment 1 or 2 wherein the water-soluble cationic N-containing polymer is present in an amount of 0.6 wt-% to 4.0 wt-%.

Embodiment 4 is the treatment composition of embodiment 3 wherein the water-soluble cationic N-containing polymer is present in an amount of 0.9 wt-% to 4.0 wt-%.

Embodiment 5 is the treatment composition of any of the preceding embodiments wherein the water-soluble cationic N-containing polymer is derived from a polymer precursor that is not cationic prior to incorporation into the treatment composition.

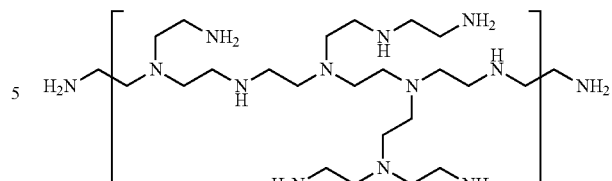

wherein n=5,000-1,000,000; and

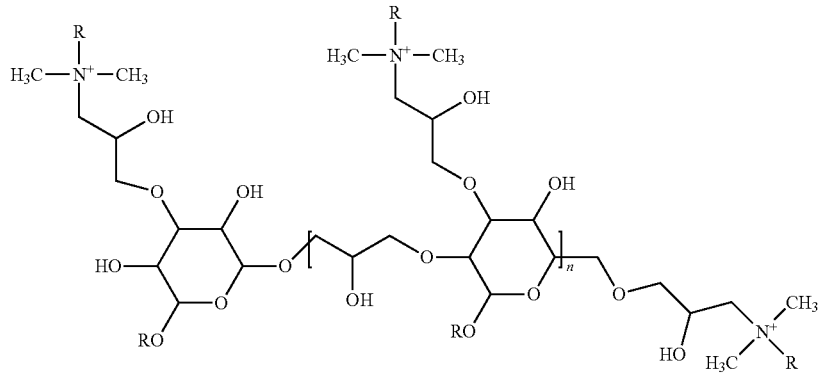

wherein n=10-1,000.

Embodiment 6 is the treatment composition of embodiment 5 wherein the water-soluble N-containing polymer or polymer precursor is selected from a (meth)acrylate copolymer having dimethylaminoethyl side groups, a polyethylenimine, a cationic-modified polysaccharide, and a combination thereof.

Embodiment 7 is the treatment composition of embodiment 6 wherein the water-soluble cationic N-containing polymer or polymer precursor is selected from:

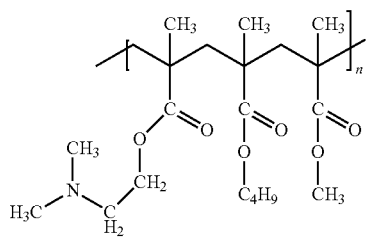

wherein n=50-2,000;

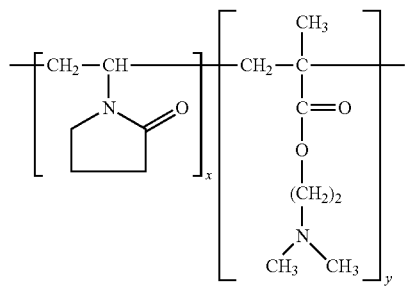

wherein x=200-20,000, and y=200-20,000;

Embodiment 8 is the treatment composition of any of the previous embodiments wherein the water-soluble cationic N-containing polymer comprises a mixture of water-soluble cationic N-containing polymers.

Embodiment 9 is the treatment composition of any of the preceding embodiments further comprising a thickener.

Embodiment 10 is the treatment composition of embodiment 9 wherein the thickener is present in an amount sufficient to provide the composition with a viscosity of 0.5 to 100 Pascal seconds at a shear rate of 1.0/second.

Embodiment 11 is the treatment composition of embodiment 9 or 10 wherein the thickener is present in an amount of at least 0.5 wt-%, and less than 2.5 wt-%.

Embodiment 12 is the treatment composition of any of embodiments 9 through 11 wherein the thickener is selected from natural gums, non-acid cellulose derivatives, inorganic fillers, alkylene oxide polymers, non-acid modified starches, and combinations thereof.

Embodiment 13 is the treatment composition of any of the preceding embodiments further comprising a calcium salt.

Embodiment 14 is the treatment composition of embodiment 13 wherein the calcium salt is present in an amount of less than 3.0 wt-% (or less than 2.0 wt-%, or less than 1.5 wt-%).

Embodiment 15 is the treatment composition of embodiment 13 or 14 wherein the calcium salt is present in an amount of at least 0.5 wt-%.

Embodiment 16 is the treatment composition of any of embodiments 13 through 15 wherein the calcium salt is selected from calcium chloride, calcium nitrate, calcium gluconate, calcium lactate gluconate, calcium acetate, hydrates thereof, and combinations thereof.

Embodiment 17 is the treatment composition of embodiment 16 wherein the calcium salt is selected from calcium chloride, calcium nitrate, hydrates thereof, and combinations thereof.

Embodiment 18 is the treatment composition of any of the preceding embodiments which has a pH of 6 to 8, or a pH of 6.5 to 7.5.

Embodiment 19 is the treatment composition of embodiment 18 which has a pH of 6 to 7, or a pH of 7.0.

Embodiment 20 is the treatment composition of any of the preceding embodiments comprising less than 5 wt-% of an organic solvent that functions as a carrier liquid (e.g., ethanol).

Embodiment 21 is the treatment composition of any of the preceding embodiments which releases at least 50% (or at least 55%, or at least 60%) of the sodium fluoride in 5 minutes or less.

Embodiment 22 is the treatment composition of any of the preceding embodiments which releases at least 85% (or at least 90%, or at least 95%) of the sodium fluoride in 10 minutes or less.

Embodiment 23 is the treatment composition of any of the preceding embodiments which releases at least 90% (or at least 95%, or at least 99%) of the sodium fluoride in 20 minutes or less.

Embodiment 24 is the treatment composition of any of the preceding embodiments which releases no greater than 90% (or no greater than 88%, or no greater than 70%) of the sodium fluoride in 1 minute or less.

Embodiment 25 is the treatment composition of any of the preceding embodiments which releases no greater than 95% (or no greater than 92%, or no greater than 75%) of the sodium fluoride in 3 minutes or less.

Embodiment 26 is the treatment composition of any of the preceding embodiments which releases no greater than 98% (or no greater than 95%, or no greater than 80%) of the sodium fluoride in 5 minutes or less.

Embodiment 27 is the treatment composition of any of the preceding embodiments which releases 100% (or no greater than 98%, or no greater than 90%) of the sodium fluoride in 10 minutes or less.

Embodiment 28 is the treatment composition of any of the preceding embodiments which releases 100% (or no greater than 99%, or no greater than 95%) of the sodium fluoride in 15 minutes or less.

Embodiment 29 is the treatment composition of any of the preceding embodiments which releases 100% (or no greater than 99%, or no greater than 98%) of the sodium fluoride in 2.0 minutes or less.

Embodiment 30 is the treatment composition of any of the preceding embodiments comprising at least 70 wt-% (or at least 80 wt-%) water.

Embodiment 31 is the treatment composition of any of the preceding embodiments comprising up to 96 wt-% (or up to 90 wt-%) water.

Embodiment 32 is the treatment composition of any of the preceding embodiments wherein the water-soluble N-containing polymer is not chemically crosslinked.

Embodiment 33 is the treatment composition of any of the preceding embodiments comprising one or more active agents in addition to sodium fluoride.

Embodiment 34 is the treatment composition of embodiment 33 wherein the one or more active agents comprise whitening agents, anticalculus agents, remineralization agents, stannous sources, antimicrobial agents, antioxidants, saliva stimulating agents, breath freshening agents, anti plaque agents, anti-inflammatory agents, $H_2$ antagonists, desensitizing agents, nutrients, proteins, or combinations thereof.

Embodiment 35 is the treatment composition of any of the preceding embodiments further comprising a flavoring agent.

Embodiment 36 is the treatment composition of any of the preceding embodiments further comprising a sweetener.

Embodiment 37 is a method of providing fluoride to a patient's tooth surface, the method comprising applying an aqueous oral care fluoride treatment composition of any of the preceding embodiments to the patient's tooth surface.

Embodiment 38 is the method of embodiment 37 wherein applying comprises painting the treatment composition on the patient's tooth surface.

Embodiment 39 is the method of embodiment 36 wherein applying comprises dispensing the treatment composition into a dental tray and attaching the tray having the treatment composition therein to the patient's tooth surface.

Embodiment 40 is the method of embodiment 39 wherein the dental tray comprises an orthodontic aligner treatment tray.

Embodiment 41 is a method of reducing the incidence of dental caries in a patient in need thereof, the method comprising applying an aqueous oral care fluoride treatment composition of any one of embodiments 1 through 39 to the patient's tooth surface.

Embodiment 42 is the method of embodiment 41 wherein applying comprises painting the treatment composition on the patient's tooth surface.

Embodiment 43 is the method of embodiment 41 wherein applying comprises dispensing the treatment composition into a dental tray and attaching the tray having the treatment composition therein to the patient's tooth surface.

Embodiment 44 is the method of embodiment 43 wherein the dental tray comprises an orthodontic aligner treatment tray.

EXAMPLES

Objects and advantages of this invention are further illustrated by the following examples, but the particular materials and amounts thereof recited in these examples, as well as other conditions and details, should not be construed to unduly limit this invention. These examples are merely for illustrative purposes only and are not meant to be limiting on the scope of the appended claims.

TABLE 1

Materials

| Names | Source | Address |
|---|---|---|
| Calcium chloride dihydrate | J. T. Baker | Center Valley, PA |
| Potassium dihydrogen phosphate ($KH_2PO_4$) | VWR | West Chester, PA |
| Sodium hydrogen phosphate ($Na_2HPO_4$) | J. T. Baker | Center Valley, PA |
| Xylitol | Roquette | Keokuk, IA |
| Sucralose | VWR | West Chester, PA |
| EUDRAGIT E100 polymer | Evonik | Darmstadt, Germany |
| Bubblegum Flavor | Footee & Jenks | Camden, NJ |
| NATROSOL 250HHX Pharm, hydroxyethyl cellulose (HEC) thickener | Ashland | Wilmington, DE |
| Sodium fluoride | Sunlit Fluo & Chemical Co | Taipei, Taiwan |
| Citric acid | Sigma Aldrich | Camden, NJ |
| NUPRO 2% Neutral sodium fluoride oral solution (fluoride gel product) 1 minute fluoride treatment with tray | Densply | York, PA |

TABLE 1-continued

Materials

| Names | Source | Address |
|---|---|---|
| PolySugaQuat-1218P (30% polymer solids) | Colonial Chemical | South Pittsburg, TN |
| Poyethyleneimine (PEI), branched, MW 10,000 | Polyscience | Niles, IL |
| VP/DMAEMA copolymer 845G | Ashland | Wilmington, DE |

Chemical Structures of Polymers

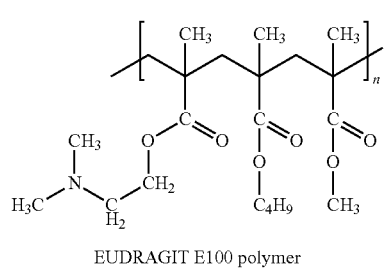

EUDRAGIT E100 polymer

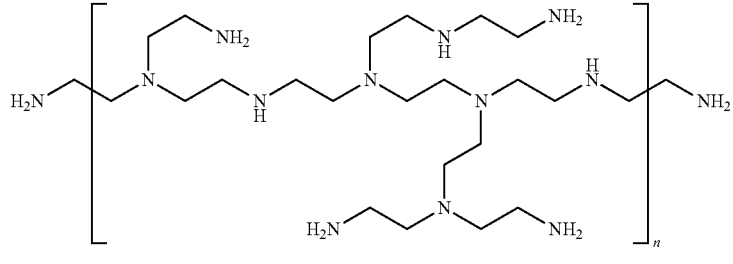

Polyscience Polyethyleneimine (PEI)

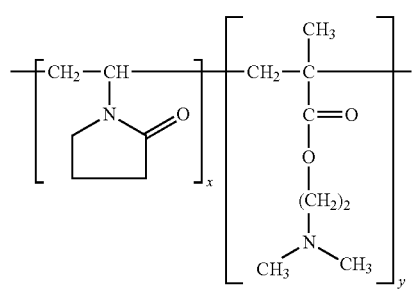

Ashland VP/DMAEMA Copolymer 845 G

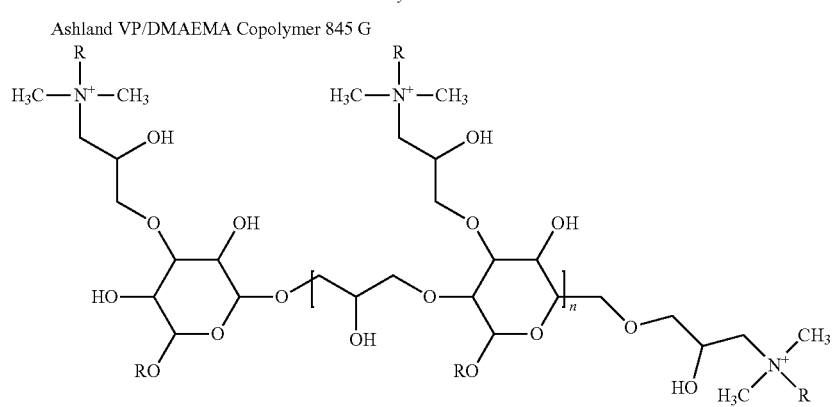

Colonial PolySugaQuat-1218P

Visual Test

Visual testing for any unwanted precipitation or polymer/water phase separation was performed. During composition preparation, the liquid composition was inspected visually for phase separation and/or white precipitation. If there was polymer aggregate or sponge-like, semi-solids gel formed due to the interaction between two different polymers in the composition, it meant that phase separation occurred and a non-uniform composition was formed.

Fluoride Release Test

Fluoride release was measured on a Mettler Toledo T70 titrator. The Cole Parmer fluoride electrode was first calibrated with parts per million (ppm) fluoride standards with TISAB III before measuring samples for fluoride release each day (Total Ionic Strength Adjustment Buffer (TISAB) III concentrate solution is for use with fluoride ion selective electrodes, Sigma Aldrich). Each Example composition was coated in a thin layer on RINZL Plastic microscope slide with 2.54 centimeters square area for both sides of the slide. The total weight of coating was about 0.045 gram. The fluoride meter titrator cup was filled with 50 milliliters of a mixture of 45 mL of MilliQ DI water and 5 mL TISAB III concentrate. The fluoride ion selective electrode was placed in the titrator cup of diluted TISAB III solution and allowed to equilibrate the meter for 30 seconds before analyzing each sample. After 30 seconds, the clamped sample was lowered into the 50 milliliters of diluted TISAB III solution. Fluoride release (mV) was measured at different time points during a 30-minute titration with Mettler Toledo T70 titrator. The fluoride release was calculated against the fluoride standards calibration curve. The average of two titrations for each example was reported.

pH Test

The pH of different compositions was measured by a pH meter of Accumet Model 15 from Fisher Scientific and a pH probe of Accumet pH probe cat #13-620-291, SN 6153081P 15 from Fisher Scientific. The meter was calibrated with standard pH solutions before measurements. A pH value was obtained by inserting the probe into the solution and waiting for 2 minutes to get the pH value.

Viscosity Test

The viscosity of the composition was measured on AR-G2 magnetic bearing rheometer from TA Instruments with parallel plate fixture at room temperature. About 1.4 mL of composition was placed between the plates and the gap of the plates was set to 1 millimeter (mm) for the measurement at room temperature. The viscosity was recorded at the shear rate of 1.0 (1/second). Two tests for each sample were conducted and the average was reported.

Fluoride Treatment Composition Preparation

Cationic Polymer Stock Solution Preparation

To convert a cationic polymer precursor to a cationic polymer the following procedure was used.

Deionized water (DI water) in an amount of 162 grams was added into a glass jar, and then 14 grams of $KH_2PO_4$ was added and mixed well to dissolve the $KH_2PO_4$ in the water. Then, 24 grams of EUDRAGIT E100 polymer was added, and the mixture was mixed for 24 hours (hrs) with a magnetic stir bar to dissolve the polymer in the water solution to form the water-soluble cationic polymer. This was the cationic polymer stock solution for EUDRAGIT E100 polymer.

DI water in an amount of 70 grams was added into a glass jar, and then 30 grams of $KH_2PO_4$ was added and mixed well to dissolve the $KH_2PO_4$ in the water. Then, 10 grams of PEI polymer was added, and the mixture was mixed for 24 hrs with a magnetic stir bar mixing to dissolve the polymer in the water solution to form the water-soluble cationic polymer. This was the cationic polymer stock solution for PEI polymer.

DI water in an amount of 88 grams was added into a glass jar, then 10 grams of VP/DMAEMA copolymer 845 was added, and the mixture was mixed for 24 hrs with a magnetic stir bar mixing to dissolve the polymer in the water solution to form the water-soluble cationic polymer. This was the cationic polymer stock solution for the VP/DMAEMA polymer.

pH 6-7 Buffer Stock Solution Preparation

Citric acid in an amount of 3.84 grams was dissolved in 200 mL of DI water, and 14.2 grams of $Na_2HPO_4$ was dissolved in 500 mL of DI water. Once both solutions were made, 465 mL of the $Na_2HPO_4$ solution was added to 150 mL of the citric acid solution. The solution was mixed well and the pH of the final solution was measured. This was the pH buffer solution, pH was 7.0.

Citric acid in an amount of 3.84 grams was dissolved in 200 mL of DI water, and 14.2 grams of $Na_2HPO_4$ was dissolved in 500 mL of DI water. Once both solutions were made, 335 mL of the $Na_2HPO_4$ solution was added to the 150 mL of the citric acid solution. The solution was mixed well and the pH of the final solution was measured. The pH was 6.39.

Fluoride Aqueous Coating Composition Preparation

Calcium chloride dihydrate was dissolved in DI water in a glass jar. Cationic polymer stock solution, sodium fluoride, DI water, xylitol, and flavorant were added into a plastic bottle and mixed well to form a solution with magnetic stirring for 30 minutes. Then, calcium chloride solution was added into the fluoride solution slowly over about 5 minutes with stirring. Further mixing was carried out for another 30 minutes. Any white precipitation during adding of the calcium chloride solution into the fluoride-containing composition was recorded. Then, other additives, such as calcium phosphate, were added as desired, and mixed well for 10 minutes. HEC NATROSOL 250HHX pharm thickener was then added and stirring was carried out for about 30 minutes. Samples were then placed on a Wheaton roller with maximum rolling speed mixing overnight to form a viscous aqueous coating composition. The samples were visually inspected for any polymer aggregate or sponge-like, semi-solids gel formation due to the interaction between two different polymers in the composition, polymer aggregate or sponge like semi-solid gel separated from water solution. which were separated from the aqueous solution.

The detailed formulations are listed in the tables below.

TABLE 2

Examples with Different Cationic Polymers

| Example | EX1 | EX2 | EX3 | EX4 |
|---|---|---|---|---|
| Cationic polymers | PolySugaQuat | PEI | VP/DMAEMA | E100 |
| Citric acid | 0.146 | 0.08 | 0.08 | 0.08 |
| DI water from pH 6.39 buffer | 24.37 | 14.63 | 14.63 | 14.63 |
| $Na_2HPO_4$ | 0.484 | 0.29 | 0.29 | 0.29 |
| Additional DI water | 20 | 25 | 25 | 25 |
| Sodium fluoride | 2 | 2.00 | 2.00 | 2.00 |
| Bubblegum flavor | 2 | 2.00 | 2.00 | 2.00 |
| Xylitol | 5 | 5.00 | 5.00 | 5.00 |
| Sucralose | 0.4 | 0.40 | 0.40 | 0.40 |
| HEC NATROSOL 250HHX pharm | 1.5 | 1.50 | 1.50 | 1.50 |
| DI water for calcium salt solution | 33.6 | 33.60 | 33.60 | 33.60 |
| Calcium chloride dihydrate | 0.5 | 0.50 | 0.50 | 0.50 |
| $KH_2PO_4$ | 0 | 4.09 | 0.00 | 1.06 |
| PolySugaQuat polymer | 3.00 | 0.00 | 0 | 0 |
| PEI polymer | 0.00 | 1.36 | 0 | 0 |
| E100 polymer | 0.00 | 0.00 | 0 | 1.79 |
| VP/DMAEMA polymer | 0.00 | 0.00 | 1.8 | 0 |
| DI water for polymer solution | 7.00 | 9.54 | 13.2 | 12.15 |
| Total | 100 | 100 | 100 | 100 |
| Total water in the composition | 84.97 | 82.77 | 86.43 | 85.38 |
| pH | 6.15 | 6.86 | 6.21 | 6.55 |
| Visual inspection | no phase separation and no precipitation | no phase separation and no precipitation | no phase separation and no precipitation | no phase separation and no precipitation |
| Viscosity (Pa · s) | 1.94 | 17.3 | 32.5 | 28.8 |

TABLE 3

Different Amounts of Thickener for Viscosity Control

| Example | EX5 | Ex6 | EX7 | EX8 |
|---|---|---|---|---|
| Thickener: | HEC at 0.5 | HEC at 1.0 | HEC at 1.2 | HEC at 2.0 |
| citric acid | 0.08 | 0.08 | 0.08 | 0.08 |
| DI water from pH 6.39 buffer | 14.63 | 14.63 | 14.63 | 14.63 |
| $Na_2HPO_4$ | 0.29 | 0.29 | 0.29 | 0.29 |
| Additional DI water | 25 | 25 | 25 | 25 |
| Sodium fluoride | 2 | 2.00 | 2.00 | 2.00 |
| Bubblegum flavor | 2 | 2.00 | 2.00 | 2.00 |
| Xylitol | 5 | 5.00 | 5.00 | 5.00 |
| Sucralose | 0.4 | 0.40 | 0.40 | 0.40 |
| HEC NATROSOL 250HHX pharm | 0.5 | 1.00 | 1.20 | 2.00 |
| DI water for calcium salt solution | 34.6 | 34.10 | 33.90 | 33.10 |
| Calcium chloride dihydrate | 0.5 | 0.50 | 0.50 | 0.50 |
| $KH_2PO_4$ | 1.06 | 1.06 | 1.06 | 1.06 |
| PolySugaQuat polymer | 0 | 0 | 0 | 0 |
| PEI polymer | 0 | 0 | 0 | 0 |
| E100 polymer | 1.79 | 1.79 | 1.79 | 1.79 |
| VP/DMAEMA polymer | 0 | 0 | 0 | 0 |
| DI water for polymer solution | 12.15 | 12.15 | 12.15 | 12.15 |
| Total | 100 | 100 | 100 | 100 |
| Total water in the composition | 86.38 | 85.88 | 85.68 | 84.88 |
| pH | 6.58 | 6.57 | 6.56 | 6.56 |
| Visual inspection | no phase separation and no precipitation | no phase separation and no precipitation | no phase separation and no precipitation | no phase separation and no precipitation |
| Viscosity (Pa · s) | 0.663 | 9.54 | 16.00 | 74.3 |

TABLE 4

Additional Examples with Different Amounts of EUDRAGIT E100 Polymer

| Example | EX9 | EX10 | EX11 |
|---|---|---|---|
| Citric acid | 0.05 | 0.05 | 0.05 |
| DI water from pH 7 buffer | 14.6 | 14.6 | 14.6 |
| $Na_2HPO_4$ | 0.35 | 0.35 | 0.35 |
| Additional DI water | 25 | 20 | 10 |
| Sodium fluoride | 2.00 | 2.00 | 2.00 |
| Bubblegum flavor | 2.00 | 2.00 | 2.00 |
| Xylitol | 5.00 | 5.00 | 5.00 |
| Sucralose | 0.40 | 0.40 | 0.40 |
| HEC NATROSOL 250HHX pharm | 1.50 | 1.50 | 1.50 |
| DI water for calcium salt solution | 33.30 | 33.30 | 33.30 |
| Calcium chloride dihydrate | 0.80 | 0.80 | 0.80 |
| $KH_2PO_4$ | 1.05 | 1.4 | 2.1 |
| E100 polymer | 1.80 | 2.40 | 3.60 |
| DI water for polymer solution | 12.15 | 16.20 | 24.30 |
| Total | 100 | 100 | 100 |
| Total water in the composition | 85.05 | 84.1 | 82.2 |
| Visual inspection | no phase separation and no precipitation | no phase separation and no precipitation | no phase separation and no precipitation |

TABLE 5

Additional Examples with Different Amounts of Polymer and Calcium Chloride

| Example | EX12 | Ex13 | EX14 | EX15 |
|---|---|---|---|---|
| Citric acid | 0.05 | 0.05 | 0.05 | 0.05 |
| DI water from pH 7 buffer | 14.6 | 14.6 | 14.6 | 14.6 |
| $Na_2HPO_4$ | 0.35 | 0.35 | 0.35 | 0.35 |
| Additional DI water | 30 | 30 | 30 | 35 |
| Sodium fluoride | 2.00 | 2.00 | 2.00 | 2.00 |
| Bubblegum flavor | 2.00 | 2.00 | 2.00 | 2.00 |
| Xylitol | 5.00 | 5.00 | 5.00 | 5.00 |
| Sucralose | 0.40 | 0.40 | 0.40 | 0.40 |
| HEC NATROSOL 250HHX pharm | 1.50 | 1.50 | 1.50 | 1.50 |
| DI water for calcium salt solution | 33.50 | 32.90 | 32.70 | 30.50 |
| Calcium chloride dihydrate | 0.60 | 1.20 | 1.40 | 0.60 |
| $KH_2PO_4$ | 0.70 | 0.7 | 0.7 | 0.56 |

TABLE 5-continued

Additional Examples with Different Amounts of Polymer and Calcium Chloride

| Example | EX12 | Ex13 | EX14 | EX15 |
|---|---|---|---|---|
| E100 polymer | 1.20 | 1.20 | 1.20 | 0.96 |
| DI water for polymer solution | 8.10 | 8.10 | 8.10 | 6.48 |
| Total | 100 | 100 | 100 | 100 |
| Total water in the composition | 86.2 | 85.6 | 85.4 | 86.58 |
| Visual inspection | no phase separation and no precipitation | no phase separation and no precipitation | no phase separation and no precipitation | no phase separation and no precipitation |

TABLE 6

Comparative Examples and Example EX16

| Example | CE1 | CE2 | CE3 | EX16 |
|---|---|---|---|---|
| Citric acid | 0.05 | 0.05 | 0.05 | 0.05 |
| DI water from pH 7 buffer | 14.6 | 14.6 | 14.6 | 14.6 |
| Na$_2$HPO$_4$ | 0.35 | 0.35 | 0.35 | 0.35 |
| Additional DI water | 0 | 0 | 35 | 0 |
| Sodium fluoride | 2.00 | 2.00 | 2.00 | 2.00 |
| Bubblegum flavor | 2.00 | 2.00 | 2.00 | 2.00 |
| Xylitol | 5.00 | 5.00 | 5.00 | 5.00 |
| Sucralose | 0.40 | 0.40 | 0.40 | 0.40 |
| HEC NATROSOL 250HHX pharm | 1.50 | 1.50 | 1.50 | 1.50 |
| DI water for calcium salt solution | 34.10 | 33.30 | 34.00 | 33.30 |
| Calcium chloride dihydrate | 0.00 | 0.80 | 0.10 | 0.80 |
| KH$_2$PO$_4$ | 2.80 | 2.80 | 0.35 | 2.45 |
| E100 polymer | 4.8 | 4.8 | 0.6* | 4.2 |
| DI water for polymer solution | 32.4 | 32.4 | 4.05 | 33.35 |
| Total | 100 | 100 | 100 | 100 |
| Total water in the composition | 81.1 | 80.3 | 87.65 | 81.25 |
| Visual inspection | polymer phase separation | polymer phase separation | no phase separation and no precipitation | slight phase separation |

*Too little cationic polymer.

TABLE 7

Comparative Examples and Example EX17: Excess Calcium Chloride Formed White Precipitation

| Example | CE4 | CE5 | CE6 | EX17 |
|---|---|---|---|---|
| Citric acid | 0.05 | 0.05 | 0.08 | 0.05 |
| DI water from pH 7 buffer | 14.6 | 14.6 | 0 | 14.6 |
| DI water from pH 6.39 buffer | 0 | 0 | 14.63 | 0 |
| Na$_2$HPO$_4$ | 0.35 | 0.35 | 0.29 | 0.35 |
| Additional DI water | 30 | 30 | 30 | 25 |
| Sodium fluoride | 2 | 2.00 | 2 | 2.00 |
| Bubblegum flavor | 2 | 2.00 | 2 | 2.00 |
| Xylitol | 5 | 5.00 | 5 | 5.00 |
| Sucralose | 0.4 | 0.40 | 0.4 | 0.40 |
| HEC NATROSOL 250HHX pharm | 1.5 | 1.50 | 1.5 | 1.50 |
| DI water for calcium salt solution | 31.1 | 29.10 | 31.1 | 32.1 |
| Calcium chloride dehydrate | 3 | 5.00 | 3 | 2.0 |
| KH$_2$PO$_4$ | 0.7 | 0.7 | 0.7 | 1.05 |
| E100 polymer | 1.20 | 1.20 | 1.20 | 1.80 |
| DI water for polymer solution | 8.10 | 8.10 | 8.10 | 12.15 |
| Total | 100 | 100 | 100 | 100 |
| Total water in the composition | 83.8 | 81.8 | 83.83 | 83.85 |
| Visual inspection | white precipitation | white precipitation | white precipitation | slight white precipitation |

TABLE 8

Percent Fluoride Release for Different Examples

| Release Time Mins | EX1 % F | EX2 % F | EX3 % F | EX4 % F | EX5 % F | EX6 % F | EX7 % F | EX8 % F | EX9 % F | Ex10 % F |
|---|---|---|---|---|---|---|---|---|---|---|
| 0   | 1.1 | 2.2 | 2.3 | 1.0 | 0.7 | 0.6 | 0.5 | 0.5 | 0.5 | 0.5 |
| 1.0 | 87  | 85  | 85  | 75  | 70  | 81  | 80  | 84  | 80  | 84  |
| 1.5 | 89  | 88  | 88  | 77  | 72  | 84  | 82  | 86  | 82  | 86  |
| 2.0 | 90  | 89  | 90  | 78  | 74  | 86  | 84  | 88  | 84  | 88  |
| 2.5 | 91  | 90  | 90  | 80  | 76  | 89  | 85  | 90  | 85  | 90  |
| 3.0 | 92  | 90  | 91  | 82  | 78  | 90  | 86  | 92  | 86  | 92  |
| 3.5 | 94  | 91  | 91  | 85  | 80  | 92  | 88  | 94  | 88  | 94  |
| 4.0 | 95  | 91  | 91  | 87  | 83  | 94  | 89  | 95  | 89  | 95  |
| 4.5 | 96  | 91  | 92  | 89  | 85  | 95  | 91  | 97  | 91  | 97  |
| 5.0 | 97  | 91  | 92  | 91  | 87  | 96  | 92  | 97  | 92  | 97  |
| 6.0 | 98  | 92  | 92  | 94  | 90  | 97  | 95  | 98  | 95  | 98  |
| 7.0 | 99  | 92  | 92  | 96  | 93  | 98  | 96  | 99  | 96  | 99  |
| 9.0 | 100 | 93  | 93  | 98  | 96  | 99  | 98  | 99  | 98  | 99  |
| 10  | 100 | 93  | 93  | 99  | 97  | 99  | 99  | 100 | 99  | 100 |
| 12  | 100 | 94  | 94  | 100 | 98  | 100 | 100 | 100 | 100 | 100 |
| 15  | 100 | 95  | 94  | 100 | 99  | 100 | 100 | 100 | 100 | 100 |
| 20  | 100 | 97  | 96  | 100 | 100 | 100 | 100 | 100 | 100 | 100 |
| 25  | 100 | 99  | 98  | 100 | 100 | 100 | 100 | 100 | 100 | 100 |
| 30  | 100 | 100 | 100 | 100 | 100 | 100 | 100 | 100 | 100 | 100 |

TABLE 9

Percent fluoride release for different examples

| Release Time Minutes | EX11 % F | Ex12 % F | EX13 % F | EX14 % F | EX15 % F | NUPRO % F | EX16 % F |
|---|---|---|---|---|---|---|---|
| 0   | 0.5 | 1.0 | 1.0 | 0.7 | 2.1 | 0.4 | 0.8 |
| 1.0 | 83  | 76  | 75  | 70  | 88  | 99  | 99  |
| 1.5 | 86  | 80  | 77  | 72  | 90  | 100 | 100 |
| 2.0 | 89  | 83  | 79  | 74  | 90  | 100 | 100 |
| 2.5 | 91  | 85  | 80  | 76  | 91  | 100 | 100 |
| 3.0 | 93  | 88  | 83  | 78  | 91  | 100 | 100 |
| 3.5 | 94  | 90  | 85  | 80  | 91  | 100 | 100 |
| 4.0 | 96  | 92  | 87  | 83  | 91  | 100 | 100 |
| 4.5 | 97  | 93  | 89  | 85  | 92  | 100 | 100 |
| 5.0 | 97  | 95  | 91  | 87  | 92  | 100 | 100 |
| 6.0 | 98  | 96  | 94  | 90  | 92  | 100 | 100 |
| 7.0 | 99  | 97  | 96  | 93  | 93  | 100 | 100 |
| 9.0 | 99  | 99  | 99  | 96  | 93  | 100 | 100 |
| 10  | 99  | 99  | 99  | 97  | 94  | 100 | 100 |
| 12  | 100 | 100 | 100 | 98  | 94  | 100 | 100 |
| 15  | 100 | 100 | 100 | 99  | 95  | 100 | 100 |
| 20  | 100 | 100 | 100 | 100 | 97  | 100 | 100 |
| 25  | 100 | 100 | 100 | 100 | 98  | 100 | 100 |
| 30  | 100 | 100 | 100 | 100 | 100 | 100 | 100 |

The complete disclosures of the patents, patent documents, and publications cited herein are incorporated by reference in their entirety as if each were individually incorporated. Various modifications and alterations to this disclosure will become apparent to those skilled in the art without departing from the scope and spirit of this disclosure. It should be understood that this disclosure is not intended to be unduly limited by the illustrative embodiments and examples set forth herein and that such examples and embodiments are presented by way of example only with the scope of the disclosure intended to be limited only by the claims set forth herein as follows.

What is claimed is:

1. An aqueous oral care fluoride treatment composition comprising:
   a water-soluble N-containing polymer present in an amount of 0.5 wt-% to 4.8 wt-%;
   sodium fluoride present in an amount of 1.0 wt-% to 2.5 wt-%;
   a water-soluble calcium salt;
   water present in an amount of at least 60 wt %; and
   a pharmaceutically acceptable buffer;
   wherein the weight percentages are based on the total weight of the aqueous composition.

2. The aqueous oral care fluoride treatment composition of claim 1, wherein the water-soluble N-containing polymer is present in an amount of 0.6 wt-% to 4.0 wt-%.

3. The aqueous oral care fluoride treatment composition of claim 1, wherein the water-soluble N-containing polymer is selected from a (meth)acrylate copolymer having dimethylaminoethyl side groups, apolyethyleneimine, a cationic-modified polysaccharide, and a combination thereof.

4. The aqueous oral care fluoride treatment composition of claim 3, wherein the water-soluble N-containing polymer is selected from:

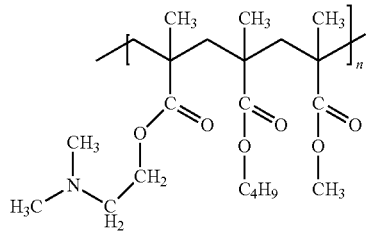

wherein n=50-2000;

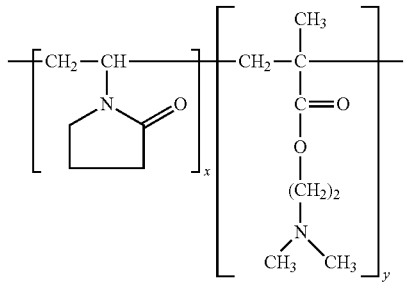

wherein x=200-20,000, and y=200-20,000;

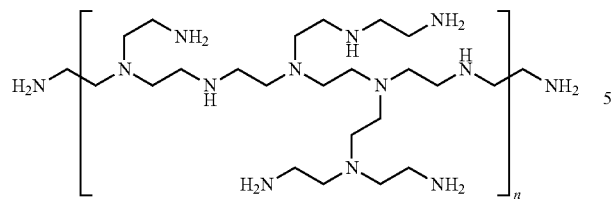

wherein n=5,000-1,000,000;

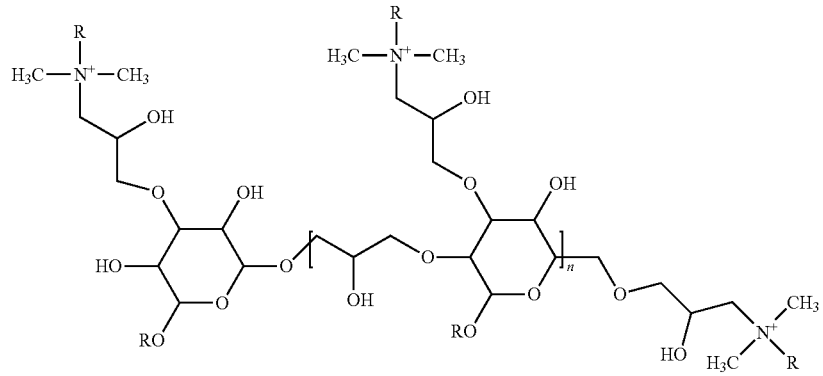

wherein n=10-1,000;
and a combinations thereof.

5. The aqueous oral care fluoride treatment composition of claim 1, further comprising a thickener.

6. The aqueous oral care fluoride treatment composition of claim 5, wherein the thickener is present in an amount sufficient to provide the composition with a viscosity of 0.5 to 100 Pascal seconds at a shear rate of 1.0/second.

7. The aqueous oral care fluoride treatment composition of claim 5, wherein the thickener is present in an amount of less than 2.5 wt-%.

8. The aqueous oral care fluoride treatment composition of claim 1, wherein the water-soluble calcium salt is selected from calcium chloride, calcium nitrate, calcium gluconate, calcium lactate gluconate, calcium acetate, hydrates thereof, and a combination thereof.

9. The aqueous oral care fluoride treatment composition of claim 1, which has a pH of 6 to 8.

10. The aqueous oral care fluoride treatment composition of claim 1, comprising less than 5 wt-% organic solvent.

11. The aqueous oral care fluoride treatment composition of claim 1, which releases at least 50% of the sodium fluoride in 5 minutes or less.

12. The aqueous oral care fluoride treatment composition of claim 1, which releases no greater than 90% of the sodium fluoride in 1 minute or less.

13. The aqueous oral care fluoride treatment composition of claim 1, which releases 100% of the sodium fluoride in 10 minutes or less.

14. The aqueous oral care fluoride treatment composition of claim 1, comprising up to 96 wt-% water.

15. A method of providing fluoride to a tooth surface of a subject, the method comprising applying an aqueous oral care fluoride treatment composition of claim 1 to the tooth surface of the subject.

16. The method of claim 15, wherein applying comprises painting the aqueous oral care fluoride treatment composition on the tooth surface of the subject.

17. The method of claim 15, wherein the applying comprises dispensing the treatment composition into a dental tray and attaching the dental tray having the aqueous oral care fluoride treatment composition therein to the tooth surface of the subject.

18. The method of claim 17, wherein the dental tray comprises an orthodontic aligner treatment tray.

19. A method of reducing the incidence of dental caries in a subject in need thereof, the method comprising applying an aqueous oral care fluoride treatment composition of claim 1 to a tooth surface of the subject.

20. The aqueous oral care fluoride treatment composition of claim 1, wherein the water-soluble calcium salt is present in an amount of 0.5 wt % to 1.5 wt % based on the total weight of the aqueous oral care fluoride composition.

21. The aqueous oral care fluoride treatment composition of claim 1, wherein the water-soluble N-containing polymer is cationic.

* * * * *